US012440334B2

(12) United States Patent
Rupp et al.

(10) Patent No.: US 12,440,334 B2
(45) Date of Patent: Oct. 14, 2025

(54) DELIVERY APPARATUS FOR A PROSTHETIC VALVE

(71) Applicant: Edwards Lifesciences Corporation, Irvine, CA (US)

(72) Inventors: Kevin D. Rupp, Irvine, CA (US); Alyssa Joy Gross, Huntington Beach, CA (US); Jun Liu, Corona, CA (US); Hamid Rafi, Irvine, CA (US); Chambory Chhe, Irvine, CA (US); Uy D. Trinh, Garden Grove, CA (US); Duc Hong Nguyen, Santa Ana, CA (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 921 days.

(21) Appl. No.: 17/478,764

(22) Filed: Sep. 17, 2021

(65) Prior Publication Data

US 2022/0000619 A1 Jan. 6, 2022

Related U.S. Application Data

(63) Continuation of application No. PCT/US2020/024130, filed on Mar. 23, 2020.

(Continued)

(51) Int. Cl.
*A61F 2/24* (2006.01)

(52) U.S. Cl.
CPC .......... *A61F 2/2439* (2013.01); *A61F 2/2418* (2013.01); *A61F 2/2436* (2013.01); *A61F 2210/0014* (2013.01)

(58) Field of Classification Search
CPC .... A61F 2/2439; A61F 2/2418; A61F 2/2436; A61F 2210/0014; A61F 2002/9511;
(Continued)

(56) References Cited

U.S. PATENT DOCUMENTS

| | | | |
|---|---|---|---|
| 519,297 | A | 5/1894 | Bauer |
| 4,035,849 | A | 7/1977 | Angell et al. |

(Continued)

FOREIGN PATENT DOCUMENTS

| | | | |
|---|---|---|---|
| DE | 19532846 | A1 | 3/1997 |
| DE | 19907646 | A1 | 8/2000 |

(Continued)

*Primary Examiner* — Jerrah Edwards
*Assistant Examiner* — Kia Xiong White
(74) *Attorney, Agent, or Firm* — Klarquist Sparkman LLP

(57) ABSTRACT

A delivery assembly comprises a delivery apparatus and a prosthetic valve releasably connected to a cord-retaining device of the delivery apparatus by a plurality of cords or tethers. The cords desirably have a multi-stranded construction formed from a plurality of strands of material. The multi-stranded construction can be, for example, a braided construction, a twisted construction, or a whip-stitch construction. The multi-stranded construction can include integral openings along opposing end portions of each cord. Each cord can extend through an aperture in an apex of the frame of the prosthetic valve or around an apex with one end portion of the cord being retained on the cord-retaining device and another end portion of the cord being retained on a slideable release member of the delivery apparatus.

18 Claims, 10 Drawing Sheets

Related U.S. Application Data

(60) Provisional application No. 62/824,710, filed on Mar. 27, 2019.

(58) Field of Classification Search
CPC ........ A61F 2/2466; A61F 2/24; A61F 2/2427; A61B 17/06166; A61B 2017/06171
See application file for complete search history.

(56) References Cited

U.S. PATENT DOCUMENTS

| | | | |
|---|---|---|---|
| 4,592,340 | A | 6/1986 | Boyles |
| 4,955,895 | A | 9/1990 | Sugiyama et al. |
| 4,994,077 | A | 2/1991 | Dobben |
| 5,059,177 | A | 10/1991 | Towne et al. |
| 5,176,698 | A | 1/1993 | Burns et al. |
| 5,192,297 | A | 3/1993 | Hull |
| 5,266,073 | A | 11/1993 | Wall |
| 5,325,845 | A | 7/1994 | Adair |
| 5,358,496 | A | 10/1994 | Ortiz et al. |
| 5,411,552 | A | 5/1995 | Andersen et al. |
| 5,554,185 | A | 9/1996 | Block et al. |
| 5,591,195 | A | 1/1997 | Taheri et al. |
| 5,599,305 | A | 2/1997 | Hermann et al. |
| 5,632,760 | A | 5/1997 | Sheiban et al. |
| 5,639,274 | A | 6/1997 | Fischell et al. |
| 5,728,068 | A | 3/1998 | Leone et al. |
| 5,749,890 | A | 5/1998 | Shaknovich |
| 5,782,809 | A | 7/1998 | Umeno et al. |
| 5,824,044 | A | 10/1998 | Quiachon et al. |
| 5,840,081 | A | 11/1998 | Andersen et al. |
| 5,908,405 | A | 6/1999 | Imran et al. |
| 5,916,147 | A | 6/1999 | Boury |
| 5,944,690 | A | 8/1999 | Falwell et al. |
| 5,961,536 | A | 10/1999 | Mickley et al. |
| 5,968,068 | A | 10/1999 | Dehdashtian et al. |
| 6,019,777 | A | 2/2000 | Mackenzie |
| 6,027,510 | A | 2/2000 | Alt |
| 6,033,381 | A | 3/2000 | Kontos |
| 6,143,016 | A | 11/2000 | Bleam et al. |
| 6,162,208 | A | 12/2000 | Hipps |
| 6,168,614 | B1 | 1/2001 | Andersen et al. |
| 6,174,327 | B1 | 1/2001 | Mertens et al. |
| 6,217,585 | B1 | 4/2001 | Houser et al. |
| 6,235,050 | B1 | 5/2001 | Quiachon et al. |
| 6,251,092 | B1 | 6/2001 | Qin et al. |
| 6,379,372 | B1 | 4/2002 | Dehdashtian et al. |
| 6,383,171 | B1 | 5/2002 | Gifford et al. |
| 6,454,799 | B1 | 9/2002 | Schreck |
| 6,458,153 | B1 | 10/2002 | Bailey et al. |
| 6,461,382 | B1 | 10/2002 | Cao |
| 6,471,672 | B1 | 10/2002 | Brown et al. |
| 6,500,147 | B2 | 12/2002 | Omaleki et al. |
| 6,514,228 | B1 | 2/2003 | Hamilton et al. |
| 6,527,979 | B2 | 3/2003 | Constantz |
| 6,579,305 | B1 | 6/2003 | Lashinski |
| 6,582,462 | B1 | 6/2003 | Andersen et al. |
| 6,652,578 | B2 | 11/2003 | Bailey et al. |
| 6,730,118 | B2 | 5/2004 | Spenser et al. |
| 6,733,525 | B2 | 5/2004 | Yang et al. |
| 6,764,504 | B2 | 7/2004 | Wang et al. |
| 6,767,362 | B2 | 7/2004 | Schreck |
| 6,830,584 | B1 | 12/2004 | Seguin |
| 6,893,460 | B2 | 5/2005 | Spenser et al. |
| 6,908,481 | B2 | 6/2005 | Cribier |
| 7,011,094 | B2 | 3/2006 | Rapacki et al. |
| 7,018,406 | B2 | 3/2006 | Seguin et al. |
| 7,018,408 | B2 | 3/2006 | Bailey et al. |
| 7,137,993 | B2 | 11/2006 | Acosta et al. |
| 7,276,084 | B2 | 10/2007 | Yang et al. |
| 7,318,278 | B2 | 1/2008 | Zhang et al. |
| 7,320,702 | B2 | 1/2008 | Hammersmark et al. |
| 7,320,704 | B2 | 1/2008 | Lashinski et al. |
| 7,374,571 | B2 | 5/2008 | Pease et al. |
| 7,393,360 | B2 | 7/2008 | Spenser et al. |
| 7,435,257 | B2 | 10/2008 | Lashinski et al. |
| 7,510,575 | B2 | 3/2009 | Spenser et al. |
| 7,585,321 | B2 | 9/2009 | Cribier |
| 7,594,926 | B2 | 9/2009 | Linder et al. |
| 7,597,709 | B2 | 10/2009 | Goodin |
| 7,618,446 | B2 | 11/2009 | Andersen et al. |
| 7,780,723 | B2 | 8/2010 | Taylor |
| 7,785,366 | B2 | 8/2010 | Maurer et al. |
| 7,959,661 | B2 | 6/2011 | Hijlkema et al. |
| 8,029,556 | B2 | 10/2011 | Rowe |
| 8,167,932 | B2 | 5/2012 | Bourang et al. |
| RE43,882 | E | 12/2012 | Hopkins et al. |
| 8,449,606 | B2 | 5/2013 | Eliasen et al. |
| 8,475,523 | B2 | 7/2013 | Duffy |
| 8,568,472 | B2 | 10/2013 | Marchand et al. |
| 9,061,119 | B2 | 6/2015 | Le et al. |
| 9,119,716 | B2 | 9/2015 | Lee et al. |
| 9,795,477 | B2 | 10/2017 | Tran et al. |
| 11,273,038 | B2 | 3/2022 | Tang et al. |
| 2001/0002445 | A1 | 5/2001 | Vesely |
| 2001/0007082 | A1 | 7/2001 | Dusbabek et al. |
| 2002/0032481 | A1 | 3/2002 | Gabbay |
| 2002/0058995 | A1 | 5/2002 | Stevens |
| 2002/0165461 | A1 | 11/2002 | Hayzelden et al. |
| 2003/0040792 | A1 | 2/2003 | Gabbay |
| 2003/0050694 | A1 | 3/2003 | Yang et al. |
| 2003/0120341 | A1 | 6/2003 | Shennib et al. |
| 2004/0093061 | A1 | 5/2004 | Acosta et al. |
| 2004/0133263 | A1 | 7/2004 | Dusbabek et al. |
| 2004/0143197 | A1 | 7/2004 | Soukup et al. |
| 2004/0186563 | A1 | 9/2004 | Lobbi |
| 2004/0186565 | A1 | 9/2004 | Schreck |
| 2004/0260389 | A1 | 12/2004 | Case et al. |
| 2005/0080474 | A1 | 4/2005 | Andreas et al. |
| 2005/0096736 | A1 | 5/2005 | Osse et al. |
| 2005/0137689 | A1 | 6/2005 | Salahieh et al. |
| 2005/0149160 | A1 | 7/2005 | McFerran |
| 2005/0203614 | A1 | 9/2005 | Forster et al. |
| 2005/0203617 | A1 | 9/2005 | Forster et al. |
| 2005/0245894 | A1 | 11/2005 | Zadno-Azizi |
| 2006/0025857 | A1 | 2/2006 | Bergheim et al. |
| 2006/0282150 | A1 | 12/2006 | Olson et al. |
| 2007/0005131 | A1 | 1/2007 | Taylor |
| 2007/0073389 | A1 | 3/2007 | Bolduc et al. |
| 2007/0088431 | A1 | 4/2007 | Bourang et al. |
| 2007/0100356 | A1 | 5/2007 | Lucatero et al. |
| 2007/0112422 | A1 | 5/2007 | Dehdashtian |
| 2007/0203575 | A1 | 8/2007 | Forster et al. |
| 2007/0219612 | A1 | 9/2007 | Andreas et al. |
| 2007/0239254 | A1 | 10/2007 | Chia et al. |
| 2007/0244546 | A1 | 10/2007 | Francis |
| 2007/0265700 | A1 | 11/2007 | Eliasen et al. |
| 2008/0065011 | A1 | 3/2008 | Marchand et al. |
| 2008/0103520 | A1 | 5/2008 | Selkee |
| 2008/0125853 | A1 | 5/2008 | Bailey et al. |
| 2008/0294230 | A1 | 11/2008 | Parker |
| 2008/0319526 | A1* | 12/2008 | Hill ...................... A61F 2/2439 623/1.12 |
| 2009/0024428 | A1 | 1/2009 | Hudock, Jr. |
| 2009/0069889 | A1 | 3/2009 | Suri et al. |
| 2009/0138079 | A1 | 5/2009 | Tuval et al. |
| 2009/0157175 | A1 | 6/2009 | Benichou |
| 2009/0192585 | A1 | 7/2009 | Bloom et al. |
| 2009/0228093 | A1 | 9/2009 | Taylor et al. |
| 2009/0276040 | A1 | 11/2009 | Rowe et al. |
| 2009/0281619 | A1 | 11/2009 | Le et al. |
| 2009/0299456 | A1 | 12/2009 | Melsheimer |
| 2009/0319037 | A1 | 12/2009 | Rowe et al. |
| 2010/0019313 | A1 | 1/2010 | Kerber et al. |
| 2010/0030318 | A1 | 2/2010 | Berra |
| 2010/0036472 | A1 | 2/2010 | Papp |
| 2010/0036473 | A1 | 2/2010 | Roth |
| 2010/0036484 | A1 | 2/2010 | Hariton et al. |
| 2010/0049313 | A1 | 2/2010 | Alon et al. |
| 2010/0076402 | A1 | 3/2010 | Mazzone et al. |
| 2010/0076541 | A1 | 3/2010 | Kumoyama |
| 2010/0082089 | A1* | 4/2010 | Quadri ...................... A61F 2/95 623/1.11 |
| 2010/0094394 | A1 | 4/2010 | Beach et al. |
| 2010/0121425 | A1 | 5/2010 | Shimada |

(56) References Cited

U.S. PATENT DOCUMENTS

| | | | |
|---|---|---|---|
| 2010/0145431 | A1 | 6/2010 | Wu et al. |
| 2010/0161036 | A1 | 6/2010 | Pintor et al. |
| 2010/0174363 | A1 | 7/2010 | Castro |
| 2010/0198347 | A1 | 8/2010 | Zakay et al. |
| 2010/0239142 | A1 | 9/2010 | Dannels et al. |
| 2010/0274344 | A1 | 10/2010 | Dusbabek et al. |
| 2010/0324647 | A1* | 12/2010 | Rincon ................. A61F 2/9526 623/1.36 |
| 2011/0015729 | A1 | 1/2011 | Jimenez et al. |
| 2011/0054596 | A1 | 3/2011 | Taylor |
| 2011/0137331 | A1 | 6/2011 | Walsh et al. |
| 2011/0160846 | A1 | 6/2011 | Bishop et al. |
| 2012/0123529 | A1 | 5/2012 | Levi et al. |
| 2012/0239142 | A1 | 9/2012 | Liu et al. |
| 2013/0030519 | A1 | 1/2013 | Tran et al. |
| 2013/0317598 | A1 | 11/2013 | Rowe et al. |
| 2014/0277340 | A1* | 9/2014 | White ....................... A61F 2/07 623/1.11 |
| 2014/0296962 | A1 | 10/2014 | Cartledge et al. |
| 2016/0045347 | A1* | 2/2016 | Smouse .............. A61M 27/008 623/23.66 |
| 2017/0065415 | A1 | 3/2017 | Rupp et al. |
| 2017/0216029 | A1* | 8/2017 | Crowley ............... A61F 2/2436 |
| 2017/0304049 | A1* | 10/2017 | Hayes .............. A61B 17/06166 |
| 2018/0153689 | A1 | 6/2018 | Maimon et al. |
| 2018/0344456 | A1 | 12/2018 | Barash et al. |
| 2019/0015203 | A1* | 1/2019 | Kheradvar ............. A61B 8/466 |
| 2019/0125534 | A1* | 5/2019 | Arcaro .................. A61F 2/2436 |
| 2019/0374342 | A1* | 12/2019 | Gregg ................... A61F 2/2439 |

FOREIGN PATENT DOCUMENTS

| | | | |
|---|---|---|---|
| EP | 0592410 | A1 | 4/1994 |
| EP | 0850607 | A1 | 7/1998 |
| FR | 2815844 | A1 | 5/2002 |
| WO | 9117720 | A1 | 11/1991 |
| WO | 9829057 | A1 | 7/1998 |
| WO | 9912483 | A1 | 3/1999 |
| WO | 0149213 | A2 | 7/2001 |
| WO | 0154625 | A1 | 8/2001 |
| WO | 0176510 | A2 | 10/2001 |
| WO | 0222054 | A1 | 3/2002 |
| WO | 0236048 | A1 | 5/2002 |
| WO | 0247575 | A2 | 6/2002 |
| WO | 02060352 | A1 | 8/2002 |
| WO | 03030776 | A2 | 4/2003 |
| WO | 03047468 | A1 | 6/2003 |
| WO | 2004019825 | A1 | 3/2004 |
| WO | 2005084595 | A1 | 9/2005 |
| WO | 2005102015 | A2 | 11/2005 |
| WO | 2006032051 | A2 | 3/2006 |
| WO | 2006111391 | A1 | 10/2006 |
| WO | 2006138173 | A2 | 12/2006 |
| WO | 2007047488 | A2 | 4/2007 |
| WO | 2007067942 | A1 | 6/2007 |
| WO | 2010121076 | A2 | 10/2010 |
| WO | 2017013187 | A1 | 1/2017 |
| WO | 2019014473 | A1 | 1/2019 |

* cited by examiner

DELIVERY APPARATUS FOR A PROSTHETIC VALVE

CROSS-REFERENCE TO RELATED APPLICATION

The present application is a continuation of PCT application PCT/US2020/024130, filed on Mar. 30, 2020, which claims the benefit of U.S. Provisional Application No. 62/824,710, filed Mar. 27, 2019, each of these applications being incorporated herein in their entireties by this reference.

FIELD

The present disclosure relates to embodiments of a delivery assembly for implanting a prosthetic valve (e.g., a prosthetic heart valve), and to methods for use of such an assembly.

BACKGROUND

Prosthetic heart valves can be used to replace or repair native heart valves that have failed or malfunctioned due to valvular disease or other such issue. Due to the risks associated with traditional open-heart surgery, implantation of such prosthetic valves and repair devices in a minimally invasive surgical procedure or a percutaneous procedure can be beneficial. For example, a replacement valve may be delivered to the implantation site by means of a flexible catheter.

A prosthetic valve can be mounted in a radially compressed position on the distal portion of a flexible catheter and advanced through the body of a patient until the valve reaches the implantation site. The prosthetic valve can then be radially expanded, for example, by self-expandable material when a delivery sheath is retracted, via balloon expansion, or another mechanical method, to its functional size within or adjacent to the defective native valve.

Challenges associated with the use of self-expandable prosthetic valves include that as the delivery sheath is retracted the prosthetic valve may expand rapidly, making it difficult to ensure controlled implantation in the proper location and, potentially, increasing the risk of trauma to the native site.

Delivery assemblies may use a single suture, or a plurality of sutures to releasably attach a prosthetic valve to the distal end of a delivery catheter. After the prosthetic valve is deployed from the sheath of the delivery catheter, the position of the prosthetic valve relative to the distal end of the delivery catheter can be maintained by the one or more sutures to permit final positioning of the prosthetic valve at the desired implantation site. Once the physician achieves proper placement of the prosthetic valve, the one or more sutures can be released from the prosthetic valve, which allows the delivery apparatus to be withdrawn from the patient's body. Challenges associated with this type of attachment technique include the possibility of entanglement between the sutures themselves, potential entanglement of the sutures with the prosthetic valve or delivery apparatus components, and potential failure of the sutures prior to final positioning of the prosthetic valve.

Accordingly, disclosed are improved transcatheter prosthetic delivery assemblies and methods for the controlled release of self-expandable prosthetic valves.

SUMMARY

This summary is meant to provide some examples and is not intended to be limiting of the scope of the invention in any way. For example, any feature included in an example of this summary is not required by the claims, unless the claims explicitly recite the features. Also, the features, components, steps, concepts, etc. described in examples in this summary and elsewhere in this disclosure can be combined in a variety of ways. Various features and steps as described elsewhere in this disclosure may be included in the examples summarized here.

Disclosed herein are embodiments of prosthetic implant delivery assemblies, as well as related methods for use of such assemblies. In some implementations, a prosthetic implant can be attached to a delivery apparatus by cords or tethers characterized by different multi-stranded constructions.

Certain embodiments of the disclosure concern a prosthetic implant delivery assembly that includes a delivery apparatus on which a prosthetic valve comprising a frame is disposed. The delivery apparatus can comprise one or more shafts, a cord-retaining device adjacent the prosthetic valve, and a plurality of twisted, wound, or braided cords connecting the frame of the prosthetic valve to the cord-retaining device.

In some embodiments, a prosthetic valve delivery assembly comprises a prosthetic valve and a delivery apparatus. The prosthetic valve comprises an expandable frame having a plurality of apices at one end of the frame. The delivery apparatus comprises a cord-retaining device comprising a plurality of circumferentially spaced tabs; one or more slideable release members extending through the cord-retaining device; a plurality of separate cords, each comprising a first end portion having a first opening and a second end portion having a second opening; and a sheath advanceable over the prosthetic valve to retain the prosthetic valve in a radially compressed state, wherein the sheath can be retracted relative to the prosthetic valve to permit radial expansion of the prosthetic valve to a radially expanded state. Each cord extends through an aperture in one of the apices or extends around one of the apices of the frame, is retained by one of the tabs extending through the opening in the respective first end portion of the cord, and is retained by one of the slideable release members extending through the opening in the respective second end portion of the cord. The one or more slideable release members can be moved axially relative to the second end portions of the cords to release the second end portions of the cords from the one or more slideable release members, thereby allowing the prosthetic valve to be released from the delivery apparatus.

In some embodiments, the cords have a multi-stranded construction formed from a plurality of strands of material.

In some embodiments, the multi-stranded construction is a braided construction. In some embodiments, the multi-stranded construction is a twisted construction. In some embodiments, the multi-stranded construction is a whip stitch construction.

In some embodiments, the plurality of strands of material are made from a polymer. In some embodiments, the polymer is an ultra-high molecular weight polyethylene.

In some embodiments, the plurality of strands of material are flexible wires.

In some embodiments, a prosthetic valve delivery assembly comprises a prosthetic valve and a delivery apparatus. The prosthetic valve comprises an expandable frame having a plurality of apices at one end of the frame. The delivery apparatus comprises a cord-retaining device along a distal end portion of the delivery apparatus; one or more slideable release members extending through the cord-retaining device; a sheath advanceable over the prosthetic valve to retain the prosthetic valve in a radially compressed state, wherein the sheath can be retracted relative to the prosthetic valve to permit radial expansion of the prosthetic valve to a radially expanded state; and a plurality of separate cords, each cord comprising a first end portion and a second end portion having an opening, wherein each cord comprises a multi-stranded construction formed from a plurality of strands of material. Each cord extends through an aperture in one of the apices or extends around one of the apices of the frame with the first end portion of the cord retained on the cord-retaining device and the second end portion of the cord retained by one of the slideable release members extending through the opening in the second end portion of the cord. The one or more slideable release members can be moved axially relative to the second end portions of the cords to release the second end portions of the cords from the one or more slideable release members, thereby allowing the prosthetic valve to be released from the delivery apparatus.

In some embodiments, the cord-retaining device comprises a plurality of tabs and the first end portion of each cord has an opening and is retained on one of the tabs extending through the opening of the first end portion of the cord.

In some embodiments, the multi-stranded construction is a braided construction. In some embodiments, the braided construction of each cord comprises the plurality of strands of material braided together along a majority of the length of the cord and the opening in the second end portion of the chord is formed by portions of the strands in the second end portion that are not braided to each other.

In some embodiments, the multi-stranded construction is a twisted construction. In some embodiments, the twisted construction of each cord comprises the plurality of strands of material in the form of a loop that is twisted along a majority of the length of the cord.

In some embodiments, the multi-stranded construction is a whip stitch construction. In some embodiments, the whip stitch construction of each cord comprises one of the strands in the form of a loop and another one of the strands wrapped around a majority of the length of the loop.

In some embodiments, a method for delivering a prosthetic heart valve, comprises inserting a distal end portion of a delivery apparatus into the vasculature of a patient, wherein a prosthetic heart valve is retained in a radially compressed state within a sheath of the delivery apparatus along the distal end portion. The prosthetic heart valve has a plurality of apices at one end thereof and is releasably connected to a cord-retaining device of the delivery apparatus by a plurality of separate cords. The delivery apparatus comprises one or more slideable release members extending through the cord-retaining device. Each cord comprises a first end portion and a second end portion having an opening, and comprises a multi-stranded construction formed from a plurality of strands of material. Each cord extends through an aperture in one of the apices or extends around one of the apices of the frame with the first end portion of the cord retained on the cord-retaining device and the second end portion of the cord retained by one of the slideable release members extending through the opening in the second end portion of the cord. The method further comprises advancing the distal end portion of the delivery apparatus and the prosthetic heart valve through the patient's vasculature to a location at or adjacent a selected implantation location and retracting the sheath of the delivery apparatus relative to the prosthetic heart valve to deploy the prosthetic heart valve from the sheath. Deploying the prosthetic heart valve from the sheath allows a distal end of the prosthetic heart valve to radially expand while a proximal end of the prosthetic heart valve remains connected to the cord-retaining device by the cords.

In some embodiments, the method further comprises retracting the one or more slideable release members relative to the cords to release the second end portions of the cords, thereby allowing the prosthetic heart valve to be released from the delivery apparatus.

In some embodiments, the multi-stranded construction is a braided construction.

In some embodiments, the first end portion of each cord has a respective opening that receives a protrusion of the cord-retaining device to retain the cord relative to the cord-retaining device.

The foregoing and other objects, features, and advantages of the disclosure will become more apparent from the following detailed description, which proceeds with reference to the accompanying figures.

DETAILED DESCRIPTION

Described herein are examples of prosthetic valve delivery assemblies and components thereof which can improve a physician's or user's ability to implant a prosthetic valve at a selected implantation location within a patient. For example, in some embodiments, a delivery apparatus can prevent a self-expandable prosthetic valve from expanding fully upon retraction of a sheath of the delivery apparatus. This allows a physician to ensure that the prosthetic valve is in the selected implantation position before allowing the prosthetic valve to expand fully. In some embodiments, for example, an arrangement of cords or tethers can be configured to secure the prosthetic valve to the delivery apparatus in such a way as to minimize the potential for the cords to become entangled with one another or with the prosthetic valve or other components of the delivery apparatus.

In some embodiments, a delivery assembly comprising a delivery apparatus and a prosthetic valve is configured to deliver and implant the prosthetic heart valve at a selected implantation site within a patient (e.g., within the native aortic valve, mitral valve, tricuspid valve or pulmonary valve). In addition to prosthetic heart valves, disclosed delivery apparatuses can be adapted to deliver and implant other types of prosthetic valves (e.g., venous valves) and various other types of prosthetic devices, such as stents, grafts, docking devices for prosthetic heart valves, heart valve repair devices (e.g., leaflet clips), embolic coils, and the like; to position imaging devices and/or components thereof, including ultrasound transducers; and to position energy sources, for example, devices for performing lithotripsy, RF sources, ultrasound emitters, electromagnetic sources, laser sources, thermal sources, and the like.

Figure 1:
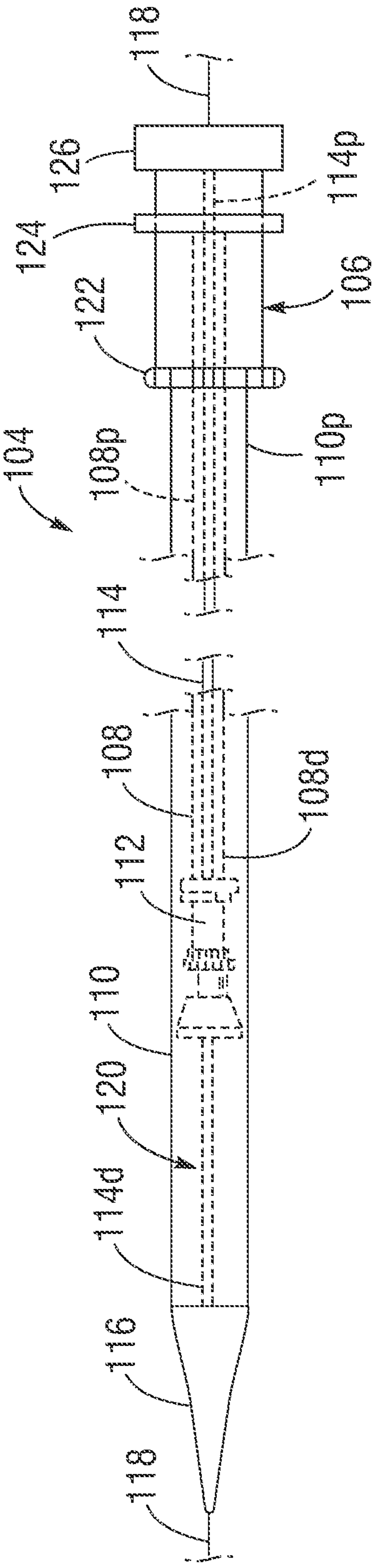
FIG. 1 is a side elevation view of an example of a delivery apparatus for delivery of a prosthetic heart valve.

In some embodiments, a prosthetic valve delivery assembly 100 can comprise the following main components: a prosthetic heart valve 102 (see e.g., FIG. 2), or another type of implantable device, and a delivery apparatus 104, an embodiment of which is shown in FIG. 1.

The delivery apparatus 104 can be constructed in a variety of ways with a variety of components. For example, the delivery apparatus can comprise one or more shafts and/or tubes, such as 1, 2, 3, 4, 5, or more. In an example embodiment shown in FIG. 1, the delivery apparatus 104 can comprise a handle 106 and a first shaft 108 extending distally therefrom. The first shaft 108 has a proximal portion 108*p* and a distal portion 108*d*. The proximal portion 108*p* of the shaft 108 can be coupled to the handle 106. In some embodiments, the distal end portion 108*d* is coupled to a cord-retaining device 112 (also referred to as a "cord manifold" or a "cord-retaining member"), which is configured to form a releasable connection with the prosthetic heart valve 102 via a plurality of cords or tethers, as discussed in detail below. In some embodiments, a second shaft 110 extends distally from the handle 106 and co-axially over the first shaft 108. In some embodiments, a third shaft 114 extends distally from the handle 106 and co-axially though the first shaft 108. The delivery apparatus can comprise a nose portion or nose cone.

In the illustrated embodiment of FIG. 1, the second shaft 110 is the outermost shaft of the delivery apparatus and therefore can be referred to as the outer shaft 110 of the delivery apparatus. In the illustrated embodiment, the third shaft 114 is the innermost shaft of the delivery apparatus and therefore can be referred to as the inner shaft 114 of the delivery apparatus. In the illustrated embodiment, the first shaft 108 is intermediate or between the innermost shaft and the outermost shaft and therefore can be referred to as an intermediate shaft. A nose cone or nose portion 116 can be coupled to (e.g., mounted on) a distal end portion 114*d* of the inner shaft 114.

FIG. 1 is a simplified schematic illustration of an exemplary delivery apparatus. Further details regarding the construction of delivery apparatuses that can be implemented in the present disclosure are disclosed in U.S. Patent Application Publication Nos. 2014/0343670, 2013/0030519, 2012/0123529, 2010/0036484, 2010/0049313, 2010/0239142, 2009/0281619, 2008/0065011, and 2007/0005131, which are incorporated by reference in their entireties.

In certain embodiments, the first, second, and third shafts 108, 110, and 114, respectively, can be configured to be moveable relative to each other, including relative axial movement (in the proximal and distal directions) and/or relative rotational movement (in the clockwise and counterclockwise directions). A guide wire 118 can extend and/or be inserted through the central lumen of the inner shaft 114 and the inner lumen of the nose cone 116 so that the delivery apparatus 104 can be advanced over the guide wire 118 inside the patient's vasculature during delivery of the prosthetic valve 102.

The delivery apparatus 104 can have a device-retaining portion 120 located between the cord-retaining device 112 and the nose cone 116. The device-retaining portion 120 can be configured to accommodate the prosthetic heart valve 102 (see e.g., FIGS. 4-6), or another type of implantable medical device, in a radially compressed state within a distal end portion 110*d* of the outer shaft 110. The distal end portion 110*d* of the outer shaft 110 can be referred to as a "delivery sheath" or "delivery cylinder" because the prosthetic valve is contained within the distal end portion 110*d* during delivery of the prosthetic valve through the patient's vasculature. The delivery sheath or delivery cylinder can be part of shaft 10 (or, optionally, can be a separate component) and can be constructed of the same material(s) and/or different material(s) compared to the rest of shaft 10. The delivery apparatus 104 is particularly suited for delivering and implanting a self-expandable prosthetic valve 102 that radially expands to its functional size under its own resiliency when deployed from the sheath 110. However, the prosthetic heart valve 102, optionally, can be a plastically expandable prosthetic valve or a mechanically expandable heart valve.

Figure 6:
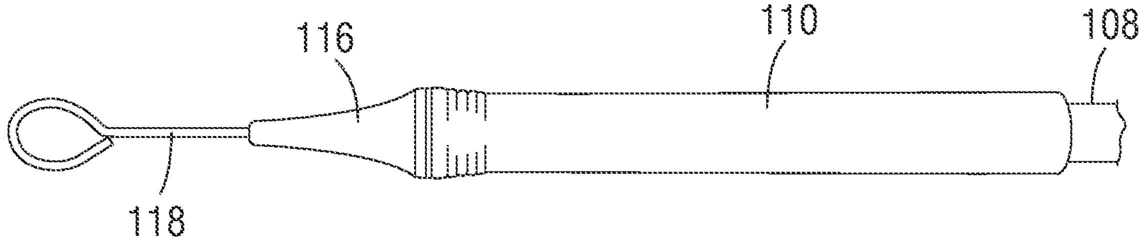
FIG. 6 is a side elevation view of the distal end portion of the example delivery apparatus of FIG. 1 shown with the sheath of the delivery apparatus fully advanced over the prosthetic heart valve frame.
Figure 7:
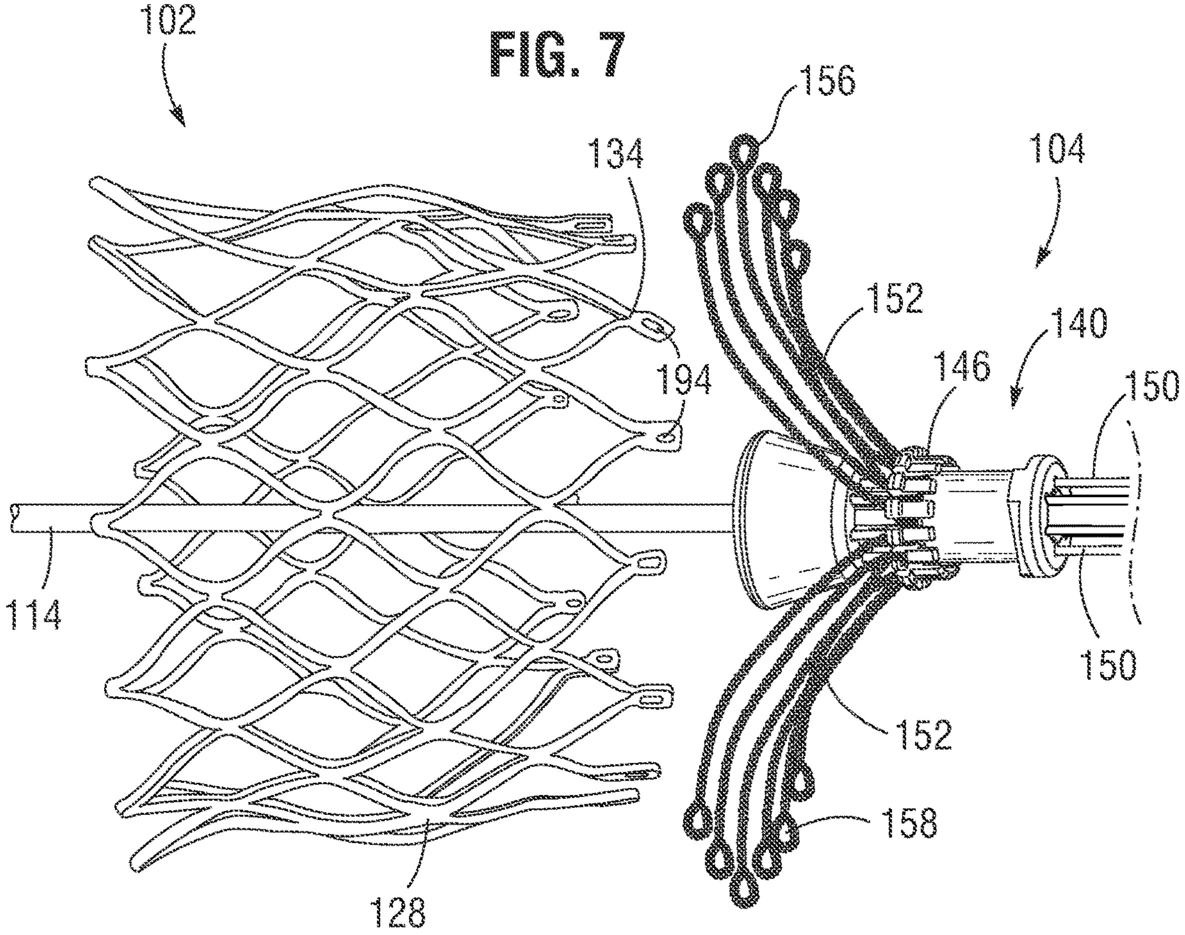
FIG. 7 is a perspective view of the distal end portion of the example delivery apparatus of FIG. 1, showing the prosthetic heart valve frame released from the delivery apparatus and fully expanded.

The outer shaft 110 and/or the delivery sheath/cylinder can be configured to move axially relative to the first shaft 108 and the third shaft 114 between a first, distal position extending over the device-retaining portion 120 and the prosthetic valve 102 for delivery through the vasculature of a patient (see e.g., FIG. 6) and a second, proximal position in which the distal end of the outer sheath is proximal to the device-retaining portion 120 to allow the prosthetic valve 102 to radially expand to its functional size at the desired implantation site (see e.g., FIG. 7).

During delivery of the prosthetic heart valve 102, the handle 106 can be maneuvered by a clinician to advance and retract the delivery apparatus 104 through the patient's vasculature.

In one embodiment, the handle 106 includes a control or a plurality of controls (such as knobs, levers, buttons, etc.) for controlling different components of the delivery apparatus 104, e.g., 1, 2, 3, 4, 5, 6 or more controls. For example, a proximal end portion 110*p* of the outer shaft 110 can be operatively coupled to a first control or knob 122, the proximal end portion 108*p* of the intermediate shaft 108 can be operatively coupled to a second control or knob 124, and a proximal end portion 114*p* of the inner shaft 114 can be operatively coupled to a third control or knob 126. In some embodiments, operation (e.g., rotational or axial movement) of the first, second, or third controls or knobs, 122, 124, 126, can cause the outer shaft 110, the intermediate shaft 108, and the inner shaft 114, to rotate about and/or slide along their longitudinal axes. In some embodiments, rotational movement of a control or knob 122, 124, or 126 can produce corresponding rotational movement of a corresponding shaft relative to the other shafts. In some embodiments, axial movement (in the proximal and distal directions) of a control or knob 122, 124, or 126 produces corresponding axial movement of a corresponding shaft relative to the other shafts. In some embodiments, rotational movement of a control or knob 122, 124, or 126 produces corresponding axial movement of a corresponding shaft relative to the other shafts.

In some embodiments, the delivery apparatus comprises one or more steering mechanisms configured to control the curvature of one or more of the shafts 108, 110, 114 to assist in steering the delivery apparatus through a patient's vasculature. For example, the steering mechanism can comprise one or more eccentrically positioned pull wires extending through a shaft and operatively connected to an adjustment mechanism located on or adjacent the handle 106. Adjustment of the adjustment mechanism is effective to change the tension of the one or more pull wires to cause the shaft to curve in a given direction, or to straighten. In one implementation, one or more pull wires extend though the outer shaft 110 and adjustment of the adjustment mechanism is effective to adjust the curvature of the distal end portion of the delivery apparatus.

Further details of the construction of the handle with controls (e.g., knobs, buttons, etc.) and the means for operating the handle and controls are described in U.S. Patent Application Publication Nos. 2013/0030519, 2009/0281619, 2008/0065011, and 2007/0005131. Different components of the delivery apparatus 104 can be controlled by different forms of controls or actuation mechanisms other than knobs, such as pull wires, buttons, joysticks, voice-controlled actuators, etc.

Figure 2:
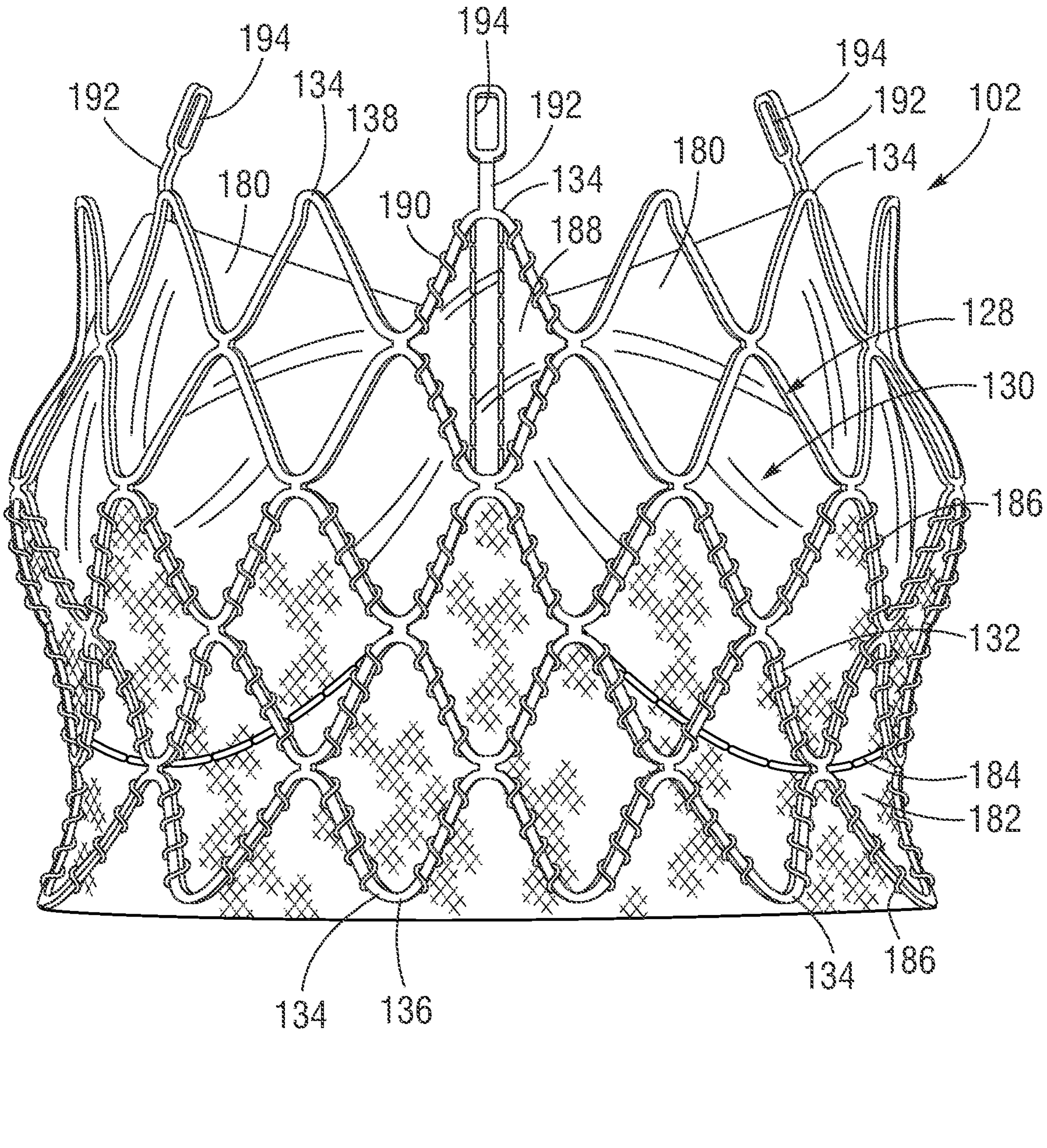
FIG. 2 is a side elevation view of an example of a prosthetic heart valve.

FIG. 2 shows a prosthetic heart valve 102, according to one embodiment, that can be used with delivery apparatus 104. The prosthetic heart valve 102 comprises a stent, or frame 128 and a valvular structure 130 (e.g., leaflets, a flap valve, etc.) supported by the frame. The frame 128 can have a plurality of interconnected struts 132 arranged in a lattice-like pattern and forming a plurality of apices 134 at the inflow and outflow ends 136, 138 of the frame 128. In one embodiment, the pattern of the frame is formed by laser cutting the pattern into a tube or sheet.

The frame 128 can include a plurality of posts 192 extending from respective apices 134 at the outflow end of the frame 128. The posts can be angularly-spaced around the frame. The frame 128 in the illustrated embodiment includes three such posts 192, although a greater or fewer number of posts can be used. In one implementation, the frame 128 can have posts extending from all the apices 134 at the outflow end of the frame. In some embodiments, each post 192 can have an eyelet or aperture 194, which can be used to form a releasable connection with the delivery apparatus 104 using one or more cords or tethers 152, as further described below.

Figure 4:
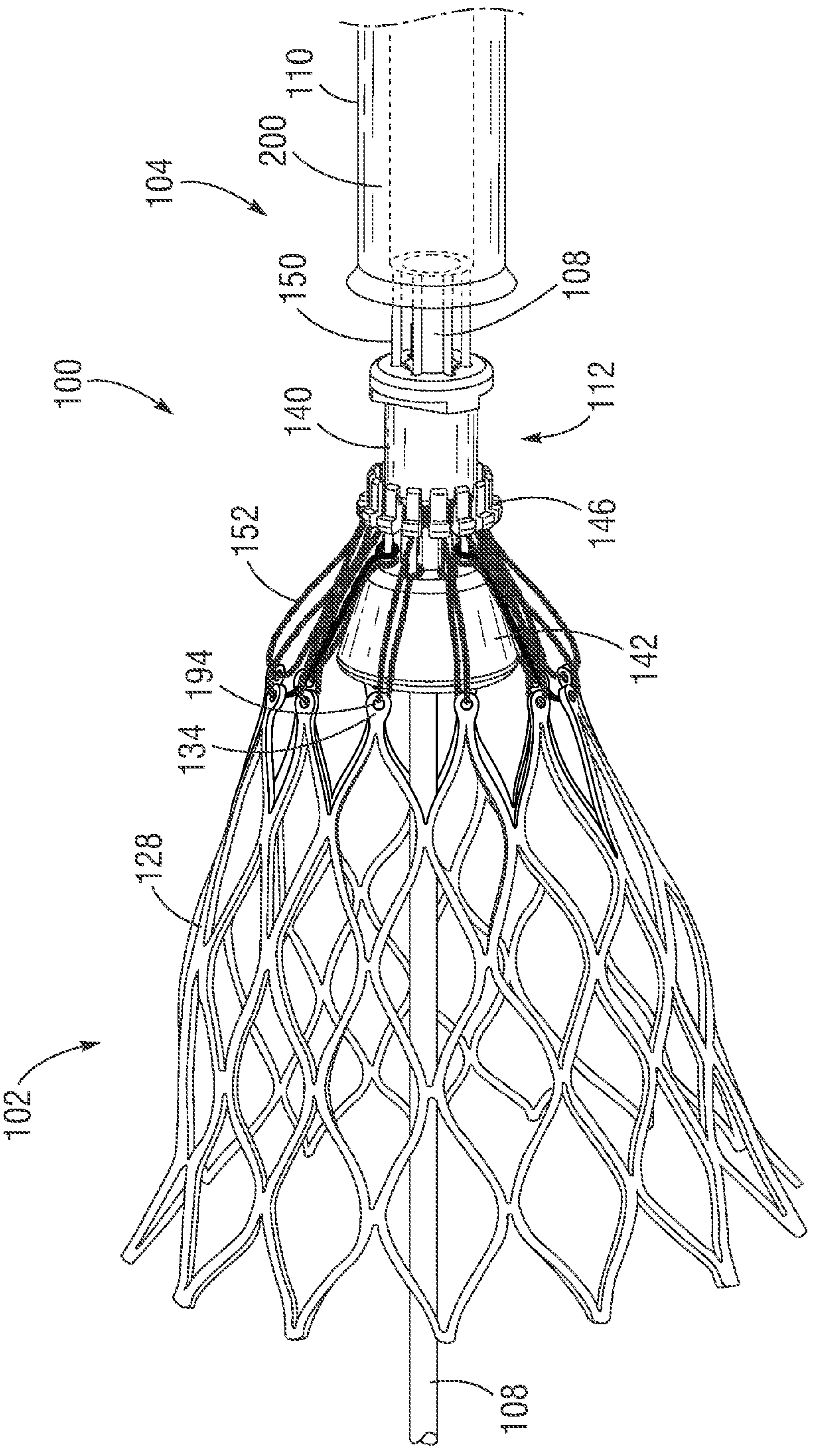
FIG. 4 is a perspective view of the distal end portion of the example delivery apparatus of FIG. 1, shown attached to a partially expanded prosthetic valve frame with a plurality of cords.

In some embodiments, as shown in FIG. 4, the frame 128 can be without posts 192 and apertures 194 can be formed in the apices 134 at the outflow end of the frame. In the embodiment of FIG. 4, all the apices 134 at the outflow end of the frame are formed with respective apertures 194, although in some embodiments, less than all the apices 134 can be formed with apertures 194. In the illustrated embodiment, the apertures 194 are formed at the outflow end of the frame so that when loaded within the delivery apparatus 104, a releasable connection can be formed between the cord-retaining device 112 and the outflow end of the frame 128 via cords 152. This arrangement facilitates delivery of the prosthetic valve 102 to the native aortic valve using a retrograde delivery approach whereby the delivery apparatus 104 is advanced through a femoral artery and the aorta to access the native aortic valve. In some embodiments, the apertures 194 (whether formed in posts 194 or in the apices 134) can be formed at the inlet end 136 of the frame 128 where other delivery apparatus configurations or other delivery techniques require apertures at the inlet end of the frame. For example, when delivering the prosthetic valve 102 to the native aortic valve via a transapical delivery approach, the inlet end 136 of the frame can be coupled to the cord-retaining device 112 via cords 152. In some embodiments, the delivery apparatus 104 can include a cord-retaining device 112 positioned distal to the prosthetic valve when loaded within the delivery apparatus, with the cord-retaining device coupled to the inlet end 136 of the frame.

In some embodiments, the prosthetic heart valve 102 is a self-expandable heart valve wherein the frame 128 is a made of a super-elastic, self-expanding material (e.g., a nickel titanium alloy such as Nitinol) as is known in the art. When used with the delivery apparatus 104, the prosthetic valve 102 can self-expand from a radially compressed state to a radially expanded state when advanced from the sheath of the delivery apparatus. In some embodiments, the frame 128 can be made of any of various suitable plastically-expandable materials (e.g., stainless steel, cobalt-chromium alloy, etc.) and the prosthetic heart valve can be expanded from a radially compressed state to a radially expanded state by inflating a balloon of the delivery apparatus or by actuating other expansion means of the delivery apparatus that produces radial expansion of the prosthetic valve.

The valvular structure 130 can comprise a plurality of leaflets 180. In some embodiments, the valvular structure comprises three leaflets 180 arranged in a tricuspid arrangement, although a greater or fewer number of leaflets 180 can be used. The leaflets 180 can be made of any various suitable materials, including natural tissue (e.g., bovine pericardium, pericardium from other sources, etc.) or synthetic materials (e.g., polyurethane). Adjacent side portions at the outflow edges (the upper edges in the drawings) of adjacent leaflets can be secured to each other to form commissures 188 of the valvular structure, which can be secured to the frame with sutures 190.

In some embodiments, the prosthetic valve 102 further includes an inner skirt 182 mounted on the inside of the frame 128. The skirt 180 helps establish a seal with the surrounding tissue after implantation. The skirt 180 can also be used to mount portions of the leaflets 180 to the frame 128. For example, in the illustrated embodiment, the inflow edges of the leaflets (the lower edges in the drawings) can be sutured to the skirt 180 along suture line 184. The skirt 180 can be connected directly to the frame 128, such as with sutures. Although not shown, the prosthetic valve 102 can include an outer skirt mounted on the outside of the frame in lieu of or in addition to the inner skirt 182 to further seal the prosthetic valve against surrounding tissue. The inner and/or outer skirts can be made of any of various suitable materials, including natural tissue (e.g., pericardium tissue) or any of various synthetic materials, which can be woven, non-woven, braided, knitted, and/or combinations thereof. In one specific implementation, the inner skirt 182 is made of a polyethylene terephthalate (PET) fabric.

Exemplary configurations of the prosthetic heart valve are further disclosed in U.S. Patent Application Publication Nos. 2013/0030519, 2012/0123529, 2010/0036484, 2010/0049313, 2010/0239142, 2009/0281619, 2008/0065011, and 2007/0005131, the disclosures of which are incorporated by reference.

Figure 3:
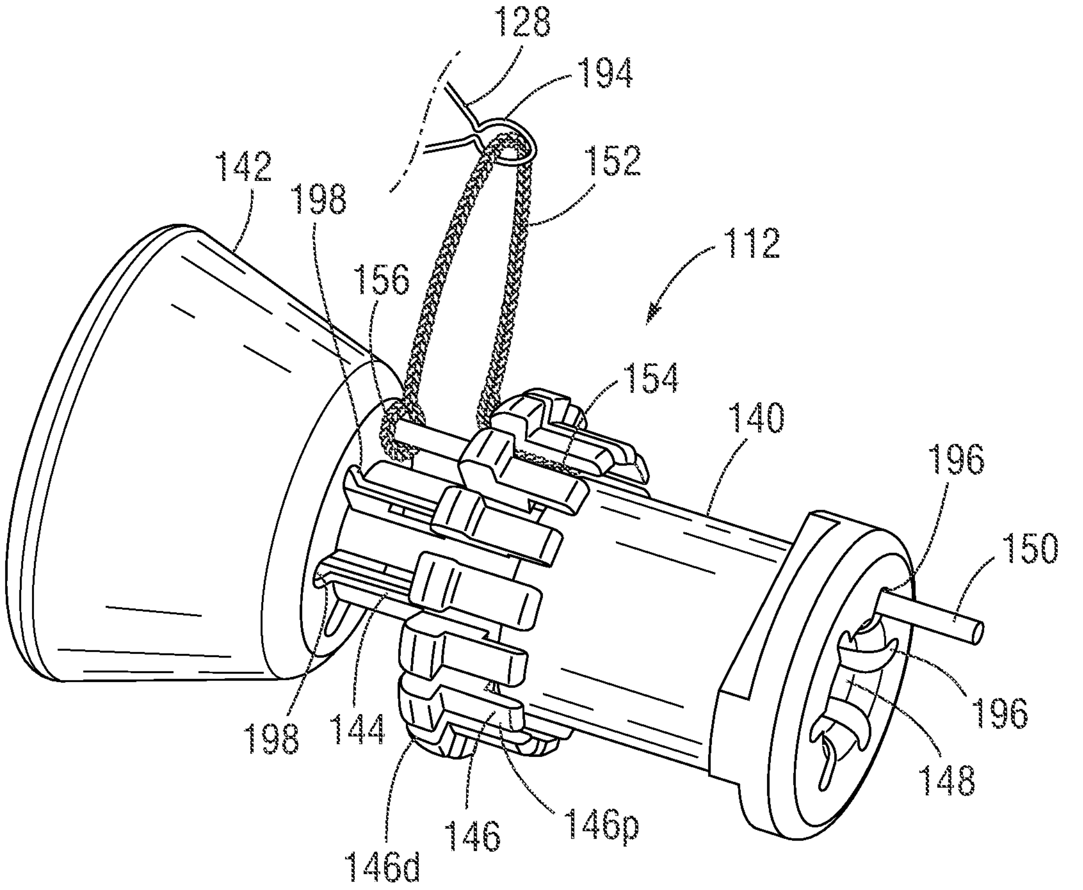
FIG. 3 is a perspective view of an example cord retaining device and an example cord that can be used in the delivery apparatus of FIG. 1.

Referring now to FIG. 3, the cord-retaining device 112 in the illustrated embodiment comprises a proximal portion 140 and a distal portion 142 axially spaced from the proximal portion 140 by a plurality of axially extending ribs 144 extending between and connecting the proximal portion to the distal portion. A plurality of radial protrusions or tabs 146 can be spaced circumferentially apart from each other around a distal end of the proximal portion 140. The proximal portion 140 can be formed with a central lumen 148 and the distal portion 142 similarly can be formed with a central lumen (not shown).

The cord-retaining device 112 can be fixedly secured to the distal end portion 108*d* of the shaft 108 using suitable techniques or mechanisms, such as via mechanical connectors, welding, a press-fit, an adhesive, etc. For example, in some embodiments, the distal end portion 108*d* of the shaft 108 can extend into the lumens of the proximal and distal portions of the cord-retaining device 112, which can be secured to the shaft 108 using any of the connection techniques described above or otherwise known. In some embodiments, the distal end portion 108*d* of the shaft 108 can be connected to the proximal end of the proximal portion 140 and need not extend into the lumen 148. The inner shaft 114 in the illustrated embodiment can extend co-axially through the lumens of the proximal and distal portions of the cord-retaining device 112 and can be movable (axially and rotationally) relative to the cord-retaining device 112. In some embodiments, the proximal and distal portions, 140, 142, of the cord retaining device 112 can be substantially cylindrical, and the plurality of axially extending ribs 144 can be disposed in a substantially cylindrical configuration between the proximal and distal portions, 140, 142. In some embodiments, as shown in FIG. 3, the proximal portion 140 can be substantially cylindrical, and the distal portion 142 can comprise a truncated conical shape, having a wider distal end tapering to a narrower proximal end. The truncated conical shape can help evenly collapse the prosthetic valve 102 into its radially compressed position.

As shown in FIG. 3, each of the tabs 146 in the illustrated embodiment can be substantially hook-shaped or L-shaped, with a relatively narrow proximal portion 146*p*, and a relatively wider distal portion 146*d*. The proximal portion 146*p* can be spaced radially outwardly from the outer surface of the proximal portion 140 of the cord-retaining device. As noted above, the frame 128 of the prosthetic heart valve 102 can be releasably coupled to the delivery apparatus 104 using one or more cords 152. Each of the cords 152 can be attached to the cord retaining device 112, such as by looping, hooking, or otherwise coupling the cord to a respective tab 146.

The cord-retaining device 112 can comprise one or more release members 150 configured to retain the cords 152 in a state connected to the frame of the prosthetic valve 102 until they are actuated by a user to release the cords 152. In illustrated embodiment, the cord-retaining device 112 includes a plurality of a release members 150 (only one of which is shown in FIG. 3 for purposes of illustration). In some embodiments, the cord-retaining device 112 can include a single release member 150 for retaining all the cords 152.

Each release member 150 can extend in a slideable manner through the proximal portion 140 of the cord retaining device 112 into the distal portion 142. The proximal portion 140 of the cord-retaining device 112 can include a plurality of openings or slots 196 sized to receive respective release members 150 and the distal portion 142 can include a plurality of openings or slots 198. The openings 196 can be angularly spaced from each other around the inner surface of the proximal portion 140 defining the lumen 148 so that the openings 196 are in communication with the lumen. Similarly, the openings 198 can be angularly spaced from each other around the inner surface of the distal portion 142 defining the lumen of the distal portion so that the openings 196 are in communication with the lumen. Each of the release members 150 is moveable in the proximal and distal directions relative to the proximal and distal portions 140, 142 of the cord-retaining device between a distal position (FIGS. 3 and 4) where each release member 150 retains a respective cord 152 and a proximal position (FIG. 7) where each release member 150 is released from a respective cord 152.

In some embodiments, each of the release members 150 can be independently moved relative to the others. In one implementation, for example, each release member 150 can extend longitudinally through the outer shaft 100 and the handle 106 of the delivery apparatus 104 and has a proximal end portion exposed for manipulation by a user, in which case a user can move a selected release member by pushing or pulling on the proximal end portion of the release member. In one implementation, each release member can extend through the outer shaft 100 and can have a proximal end portion operatively connected to a respective actuator or control (e.g., a knob, etc.) on the handle 106 that can be actuated by a user to produce axial movement of the release member.

In some embodiments, the release members 150 can be configured to be moved together as a unit. For example, as depicted in FIG. 4, the proximal ends of the release members 150 can be connected to a common shaft 200 that extends co-axially through the outer shaft 110. The proximal end portion of the shaft 200 can be exposed at the proximal end of the delivery apparatus 104 for manipulation by a user, it can be operatively connected to an actuator (e.g., a knob) on the handle 106 that is operable to control axial movement of the shaft 200. In either case, axial movement of the shaft 200 (in the proximal and distal directions) is effective to cause corresponding axial movement of all the release members 150.

Figure 8:
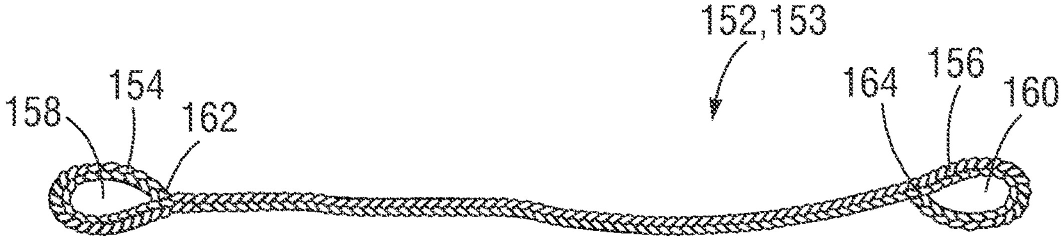
FIG. 8 is a top plan view of an example of a cord having a braided construction.

As best shown in FIGS. 3 and 4, when the prosthetic valve 102 is coupled to the cord-retaining device 112, each of the cords 152 extends through an aperture 194 of the frame 128 and has a first end portion 154 secured to one of the tabs 146 and a second end portion 156 secured to one of the release members 150. Referring also to FIG. 8, the first and second end portions 154, 156 can comprise first and second openings 158, 160, respectively, such that the first and second end portions 154, 156 form respective closed loops at opposite ends of the cord. The openings 158, 160 in the cord can formed in various ways, which are further described below.

In the illustrated embodiment, as best shown in FIG. 4, each apex 134 of the frame 128 is secured to the cord-retaining device 112 with a respective cord 152 extending through the aperture 194 of the corresponding apex.

The first loop 154 can be secured to a respective tab 146 by sliding the first loop 154 over the proximal portion 146*p* and around the distal portion 146*d* of the tab. The opening 158 of the first loop 154 is sized to fit snugly around the distal portion 146*d*, as shown in FIG. 3, which secures that end of the cord to the tab. The second loop 156 is placed over a respective release member 150 and is retained thereon between the proximal and distal portions 140, 142, respectively, of the cord-retaining device when the release member is in the distal position. When the release member 150 is moved to the proximal position, the second loop 156 can slide off the release member 150, thereby allowing the frame 128 of the prosthetic valve to be released from the cord.

In some embodiments, the first end portions 154 of cords 152 need not be in the form of loops and need not be retained on the tabs 146. Instead, the first end portions 154 of the cords 152 can be affixed to the proximal portion 140 of the cord-retaining device, such as with an adhesive and/or mechanical connectors.

The prosthetic valve 102 can be coupled to the cord-retaining device 112 using any number of cords 152. Desirably, at least three cords 152 are used to balance the attachment of the frame 128 to the cord-retaining device 112. In particular embodiments, the number of cords 152 is equal to the number of apices 134 of the frame 128 and the number of tabs 146 on the cord-retaining device 112. That way, when the prosthetic valve 102 is coupled to the cord-retaining device 112, a separate cord 152 extends through each aperture 194 of the frame and is secured to one of the tabs 146. In the illustrated embodiment, the number of release members 150 is less than the number of cords 152. As such, the second loops 156 of multiple cords 152 can be placed on a single release member 150.

It should be noted that the number of the cords, as well as the number of the tabs 146 and release members 150 can be varied as desired for different applications. In some embodiments, for example, the prosthetic valve 102 can be coupled to the cord-retaining device 112 with a number of cords 152 that is less than the number of apices 134 on the frame 128 so that there are some apices 134 that are not retained by a cord. In some embodiments, the number of tabs 146 is less than the number of cords 152 so that the first loops 154 of multiple cords 152 can be placed around a single tab 146. In some embodiments, the number of release members 150 can be equal to the number of cords 152 so that the second loop 156 of only one cord 152 is retained on each release member. In this manner, if each release member is independently moveable relative to the others, then the release of each cord 152 from its corresponding release member 150 and aperture 194 on the frame 128 can be independently controlled during deployment of the prosthetic valve.

It also should be noted that one or more of the cords 152 need not extend through apertures 194 in the frame 128 of the prosthetic valve. Instead, when the prosthetic valve is coupled to the cord-retaining device 112, a cord 152 can extend through the space between two struts 132 that form an apex 134 at one end of the frame such that the cord wraps around the apex 134 and has one end secured to a tab 146 and another end secured to a release member 150. For example, the embodiment of the frame 128 shown in FIG. 2 has only three apertures 194. The frame 128 of FIG. 2 can be coupled to the cord-retaining device 112 with cords 152 extending through the apertures 194 and with cords 152 wrapped around the apices 134 without apertures. In some embodiments, the frame 128 need not be formed with any apertures 194, in which case the prosthetic valve can be coupled to the cord-retaining device 112 with one or more cords wrapped around one or more of the apices 134 at one end of the frame 128. In some embodiments, less than all the apices 134 are connected to the cord-retaining device 112 with respective cords 152. For example, the frame 128 of FIG. 2 can be connected to the cord-retaining device 112 only with cords extending through the apertures 194 in the posts 192 and the remaining apices between the posts 192 can remain unconnected to the cord-retaining device 112

Figure 5:
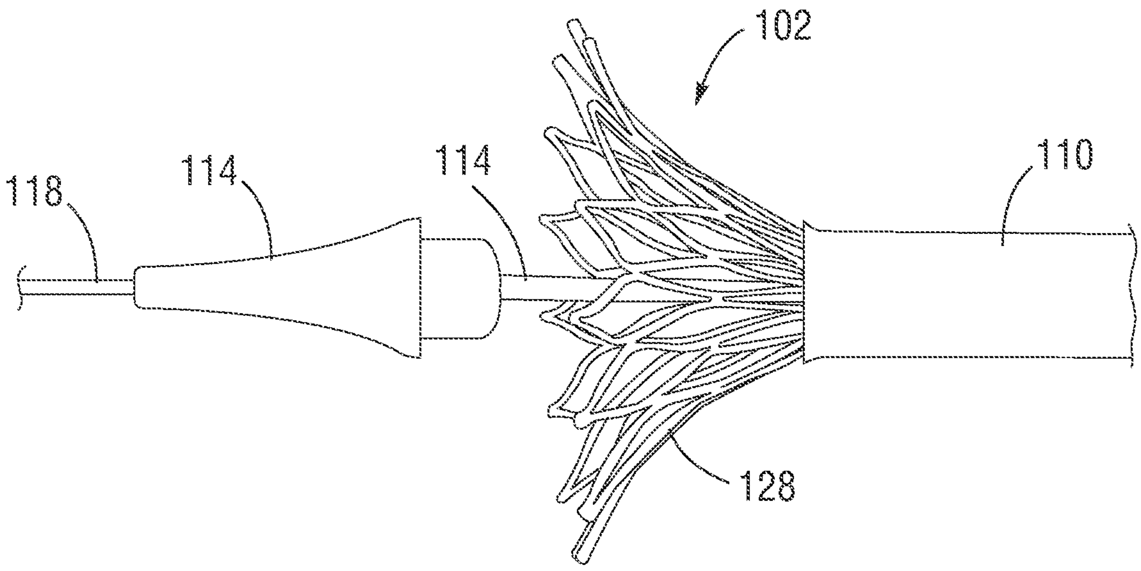
FIG. 5 is a side elevation view of the distal end portion of the example delivery apparatus of FIG. 1 shown with a sheath of the delivery apparatus advanced over a portion of the prosthetic heart valve frame.

Returning again to FIG. 4, loading of the prosthetic valve 102 within the delivery apparatus will now be described. The frame 128 of the prosthetic valve is coupled to the cord-retaining device 112 with one or more cords 152 as previously described. In FIGS. 4, 5 and 7, only the bare frame 128 is shown and the soft components of the prosthetic valve 102 (e.g., the leaflets and the skirt) are omitted for purposes of illustration. Desirably, although not necessarily, a releasable connection is formed between each and every apex 134 at one end of the frame 128 (e.g., the outflow end in the illustrated example) and the cord-retaining device 112 with a separate cord 152. Desirably, although not necessarily, the length of the cords 152 are selected such that the secured end of the frame is held in an at least partially radially compressed state by the cords, as depicted in FIG. 4.

After securing the end of the frame 128 with the cords 152, the outer shaft 110 can be advanced distally over the cord-retaining device 112, the cords 152, and the frame 128, causing the frame to collapse to a radially compressed state under the force of the outer shaft. The outer shaft 110 can be advanced distally until the distal end of the shaft 110 abuts the nose cone 116 to fully enclose the prosthetic valve 102, as depicted in FIG. 6. As the outer shaft 110 is advanced over the cords 152, tension in the cords 152 increases, which helps draw the apices 134 of the frame radially inwardly into the interior of the outer shaft 110. As noted above, the frusto-conical shape of the distal portion 142 of the cord-retaining device 112 facilitates advancement of the outer shaft 110 over the adjacent apices 134 connected to the cords 152 and collapses that end of the frame in an even and predictable manner.

When the prosthetic valve 102 is in the delivery state within the outer shaft 110, the apices 134 connected to the cords 152 can be held against the distally facing surface of the distal portion 142 of the cord-retaining device 112. In some embodiments, the apices 134 connected to the cords 152 can be retained at a location along the outer side surface of the distal portion 142 or at a location between the distal portion 142 and the proximal portion 140.

After loading the prosthetic heart valve 102 within the delivery apparatus 104 as described above, the delivery apparatus can be inserted and the valve delivery transvascularly. For example, the delivery apparatus can be inserted in the vasculature of a patient and advanced through the patient's vasculature to the desired implantation site (e.g., through a femoral artery and the aorta when delivering the prosthetic valve 102 in a retrograde delivery approach to the native aortic valve).

Once the prosthetic valve 102 is delivered to a selected implantation site within the patient, the delivery sheath and/or outer shaft 110 can be retracted in order to deploy the prosthetic valve 102. In some embodiments, as the delivery sheath and/or shaft 110 is retracted, the prosthetic valve radially self-expands under the resiliency of the frame 128, as depicted in FIG. 5. After the delivery sheath and/or shaft 110 is fully retracted from the prosthetic valve 102, the prosthetic valve is still attached to the delivery apparatus 104 by the cords 152, as depicted in FIG. 4. While still attached to the delivery apparatus, the physician can manipulate the delivery apparatus (e.g., by moving it in the proximal and distal directions and/or rotating it) to adjust the position of the prosthetic valve relative to the desired implantation location.

If desired, the delivery sheath and/or outer shaft 110 can be advanced back over the prosthetic valve 102 to fully or partially recapture the prosthetic valve (bring the prosthetic valve back within the outer shaft) to facilitate re-positioning of the prosthetic valve. For example, after crossing the native aortic valve leaflets in a retrograde delivery approach and deploying the prosthetic valve, it may be desirable to recapture the prosthetic valve back within the delivery sheath and/or outer shaft, retract the delivery apparatus to bring the prosthetic valve back within the aorta, and then advance the prosthetic valve back across the native aortic valve leaflets, and deploy the prosthetic valve from the delivery sheath and/or outer shaft.

Figure 9:
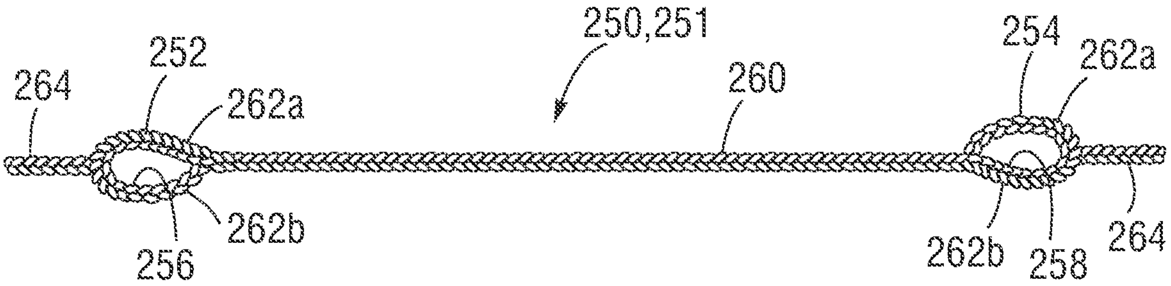
FIG. 9 is a top plan view of another example of a cord having a braided construction.

Once the prosthetic valve is deployed from the delivery sheath and/or outer shaft and positioned at the desired implantation location, the release members 150 can be retracted to free the second end portions 156 of the cords 152. In some cases, the cords 152 slide outwardly from the apertures 194 and free themselves from the frame 128 by virtue of the self-expanding frame 128 further expanding when the release members 150 are retracted. In some cases, the physician can slightly retract the delivery apparatus 104, which in turn pulls the cords 152 proximally relative to the frame 128 to pull them out of the apertures 194, as depicted in FIG. 9.

As noted above, the orientation of the prosthetic valve can be reversed such that the inflow end of the prosthetic valve is the proximal end and the outflow end of the prosthetic valve is the distal end when coupled to the delivery apparatus. This can facilitate delivery of the prosthetic valve to different implantation locations (e.g., the native aortic, pulmonary, mitral, and tricuspid annuluses) and/or for various delivery approaches (e.g. antegrade, transseptal, transventricular, transatrial).

The cords 152 can be made of any of various suitable biocompatible materials for use within a patient's body. In particular embodiments, a cord 152 can comprise a multifilament or multi-strand cord formed from braiding, weaving, knitting, twisting, and wrapping a plurality of filaments or strands together. The filaments or strands can comprise polymeric fibers, such as ultra-high molecular weight polyethylene, nylon, polyester, and/or aramid, or flexible wires (e.g., metal wires). Described below are various ways of forming a multifilament or multi-strand cord for use in coupling a prosthetic valve 102 to the cord-retaining device 112 of the delivery apparatus 104.

FIG. 8 shows a cord 152 comprising a multifilament braided structure 153 comprising loops 154, 156 defining openings 158, 160 at opposite ends of the cord. The braided structure 153 can be formed by braiding together multiple filaments. To form the loops 154, 156, the end portions of the braided structure can be folded back and secured against adjacent sections of the braided structure at locations 162, 164. The adjacent portions of the braided structure can be secured to each other at locations 162, 164 using, for example, an adhesive and/or welding, or other attachment means.

FIG. 9 shows an example of a cord 250 comprising a multifilament braided structure 251. The cord 250 has first and second end portions 252 and 254, respectively, having openings 256, 258, respectively. The cord 250 can be formed by braiding together multiple filaments or strands of material. The openings 256, 258 can be integrally formed within the end portions 252, 254 during the braiding process by separating or isolating a first set of one or more filaments from a second set of one or more filaments along the end portions 252, 254.

In the illustrated embodiment, the majority of the length of the cord forms a fully braided section 260 (that is, all the filaments form part of the braid) while along each end portion 252, 254, two or more filaments form a first braided section 262*a* and two or more filaments form a second braided section 262*b* separated or isolated from the first braided section 262*a* to form openings 256, 258. At the outer ends of the cord, the first and second braided sections 262*a*, 262*b* come together to form braided tail portions 264 that incorporate all the filaments in the braid.

The number of filaments, the grade of the filaments (e.g., linear density), the braid density (e.g., picks per inch), the filament material, and braiding pattern can vary depending on the application. In particular embodiments, a braided cord 152, 250 can be formed from three or more filaments, four or more filaments, five or more filaments, etc. In certain embodiments, the braided cords are formed from six to 48 filaments, with eight filaments being a specific example. In certain embodiments, the linear density of the filaments can range from about 10 dtex to about 110 dtex. In certain embodiments, the braiding density can range from about 25 ppi to about 200 ppi.

In a specific example, a braided cord 152, 250 is formed from braiding together eight filaments of 55 dtex ultra-high molecular weight polyethylene using a 1 over 2 full load pattern having 120 ppi to form a cord having a diameter approximately the size of a 2-0 suture. A braided cord 250 formed has an ultimate tensile strength of at least 30N when tested with a 0.010" steel wire loop pulled through each opening 256, 258.

Figure 10A:
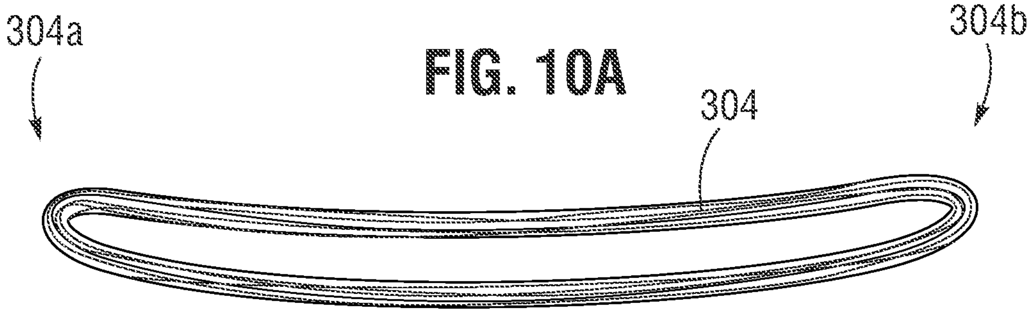
FIG. 10A-10C illustrate one example of a method for forming a cord having a twisted construction.
Figure 10B:
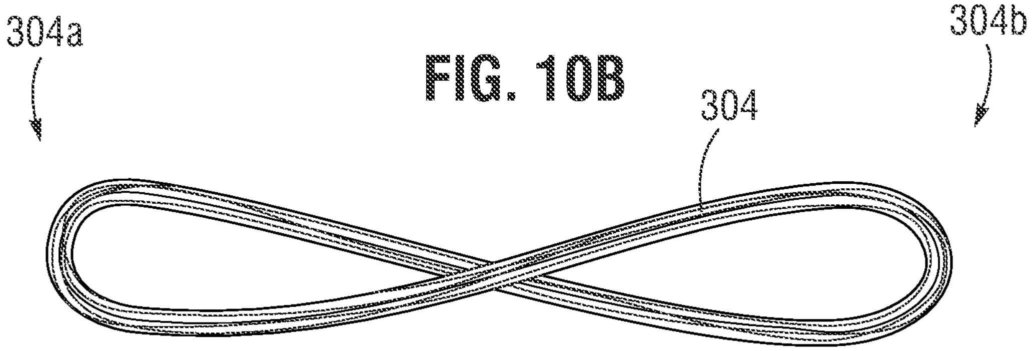
Figure 10C:
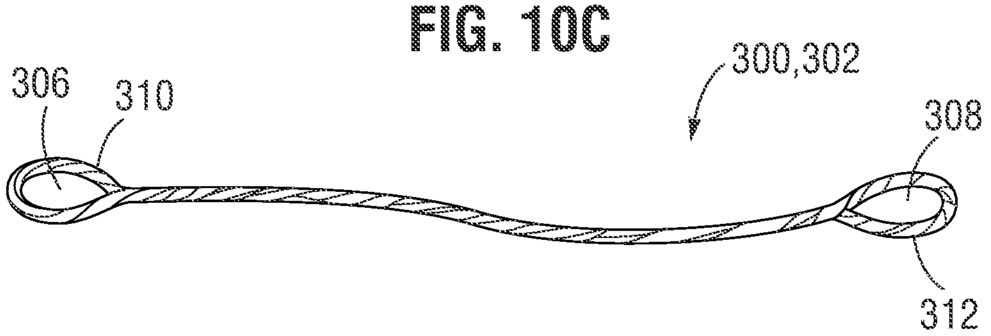

In some embodiments a cord can comprise a twisted construction shown in FIG. 10C. FIGS. 10A-10C illustrate a method for forming a cord 300 with a twisted construction 302. The method comprises providing a multi-stranded loop of material 304 (a set of strands or filaments in the form of a loop) as shown in FIG. 10A, and twisting first and second ends of the loop, 304*a*, 304*b* in opposing directions as shown in FIG. 10B until first and second openings 306, 308, respectively, of a selected size are defined along opposing end portions 310, 312 of the formed cord 300, as shown in FIG. 10C. In some embodiments, the loop 304 is twisted along the majority of the length of the cord. In some embodiments, the filaments are retained in the twisted construction 302 either a heat set (causing the filaments to bond to each other) or a coating. In some embodiments, the multi-stranded loop 304 comprises two or more strands or filaments. The multi-stranded loop 304 comprises a plurality of strands twisted together to create a desired strength and/or thickness.

Figure 11A:
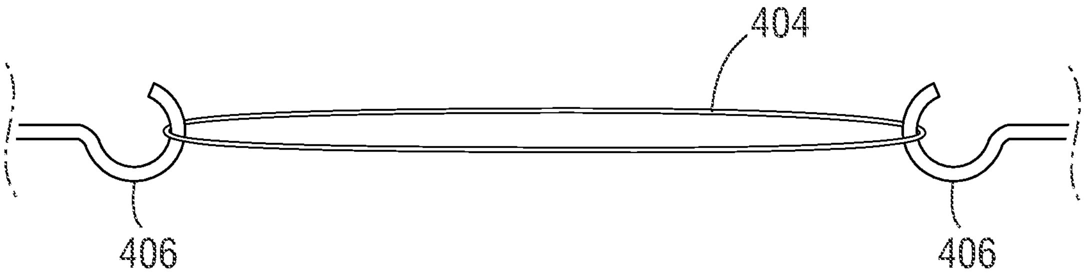
FIGS. 11A-11C illustrate one example method for forming a cord having a whip-stitch construction.
Figure 11B:
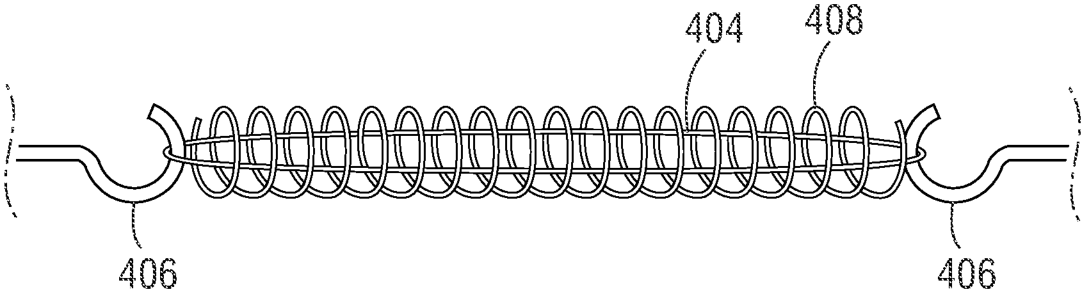
Figure 11C:
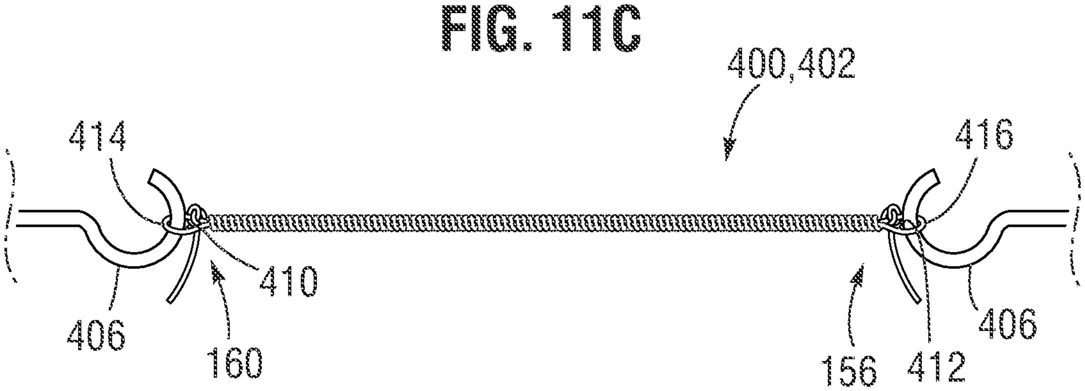

In one embodiment, a cord can comprise a whip-stitch construction as shown in FIG. 11C. FIGS. 11A-11C illustrate a method for forming a cord 400 with a whip-stitch construction 402. The method comprises providing a loop of material 404 as shown in FIG. 11A comprising one or more strands or filaments (one in the illustrated embodiment). The ends of the loop 404 can be placed around two fixtures, such as in the form of hooks 406, that hold the loop relatively taught during the forming process. As shown in FIG. 11B, the loop 404 is wrapped with a wrapping strand or filament 408 (or a multi-stranded length of the material) in a whip stitch pattern along the majority of the length of the loop. The wrapping strand 408 is wrapped tightly around the loop 404 except along end portions 414, 416 so as to form first and second openings, 410, 412, of a selected size at opposing ends of the cord 400, as shown in FIG. 11C. The ends of the wrapping strand 408 can be secured to the end portions 414, 416 of the loop 404, such as by tying off the ends of the wrapping strand 408 to the end portions of the loop 404 (as shown in FIG. 11C), by welding, and/or an adhesive (e.g., a UV-curable adhesive), or other attachment means.

In some embodiments, the loop 404 and the wrapping strand 408 are single lengths of 4-0 or 5-0 ultra-high molecular weight polyethylene suture. In some embodiments, the loop 404 can comprise a plurality of filaments and the wrapping strand can comprise a plurality of filaments to create a desired strength and/or thickness.

In some embodiments, a single strand can be used to create a cord having a whip-stitch construction. For example, the single strand can be formed into a loop and tied with a knot, and the remaining length still attached to the knot can then be used to wrap around the loop in a whip-stitch pattern, leaving two openings along opposing end portions of the loop.

The closed body construction and small openings of the multi-stranded cords in the braided, twisted, and whip-stitch constructions reduce the risk that the cords may become entangled with one another or with the prosthetic valve or other components of the delivery assembly during the process of attaching or releasing the prosthetic valve.

Figure 12:
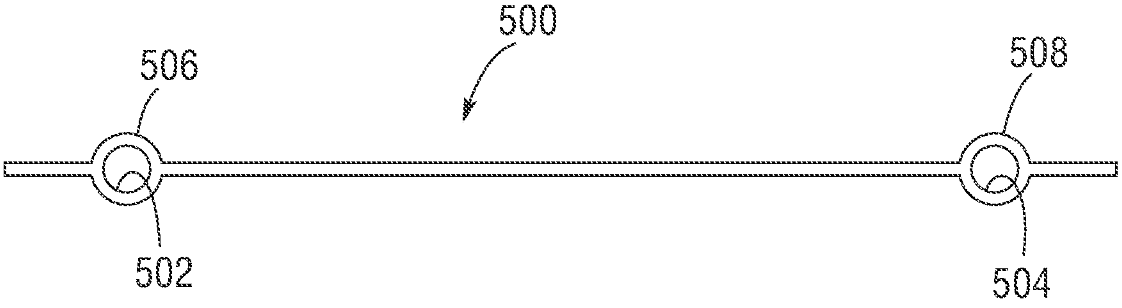
FIG. 12 is a top plan view of an example of a cord.

In one embodiment, a cord or tether for connecting a prosthetic valve to the cord-retaining device 112 can comprise a piece of material (e.g., a piece of fabric, such as a PET fabric)) that is cut (e.g., laser cut) so as to have the overall shape similar to that of the cord 152 shown in FIG. 8 or the cord 250 shown in FIG. 9. For example, FIG. 12 shows one example of a cord or tether 500 that can be cut from a piece of material, such as a biocompatible fabric (e.g., a PET fabric). The piece of material is cut to have integral openings 502, 504 along opposing end portions 506, 508 of the cord. In some embodiments, a cord or tether 500 can be formed from multiple layers of material (e.g., multiple layers of fabric, such as PET fabric) that are cut into the same shape and layered on top of each other. The layers of materials can be bonded to each other (e.g., using an adhesive) to form a laminate that has integral openings along opposite end portions of the cord.

General Considerations

For purposes of this description, certain aspects, advantages, and novel features of the embodiments of this disclosure are described herein. The described methods, systems, and apparatus should not be construed as limiting in any way. Instead, the present disclosure is directed toward all novel and non-obvious features and aspects of the various disclosed embodiments, alone and in various combinations and sub-combinations with one another. The disclosed methods, systems, and apparatus are not limited to any specific aspect, feature, or combination thereof, nor do the disclosed methods, systems, and apparatus require that any one or more specific advantages be present or problems be solved.

Features, integers, characteristics, compounds, chemical moieties, or groups described in conjunction with a particular aspect, embodiment or example of the disclosure are to be understood to be applicable to any other aspect, embodiment or example described herein unless incompatible therewith. All of the features disclosed in this specification (including any accompanying claims, abstract, and drawings), and/or all of the steps of any method or process so disclosed, may be combined in any combination, except combinations where at least some of such features and/or steps are mutually exclusive. The disclosure is not restricted to the details of any foregoing embodiments. The disclosure extends to any novel one, or any novel combination, of the features disclosed in this specification (including any accompanying claims, abstract, and drawings), or to any novel one, or any novel combination, of the steps of any method or process so disclosed.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods, systems, and apparatus can be used in conjunction with other systems, methods, and apparatus.

As used herein, the terms "a," "an," and "at least one" encompass one or more of the specified element. That is, if two of a particular element are present, one of these elements is also present and thus "an" element is present. The terms "a plurality of" and "plural" mean two or more of the specified element.

As used herein, the term "and/or" used between the last two of a list of elements means any one or more of the listed elements. For example, the phrase "A, B, and/or C" means "A," "B," "C," "A and B," "A and C," "B and C," or "A, B, and C."

As used herein, the term "coupled" generally means physically coupled or linked and does not exclude the presence of intermediate elements between the coupled items absent specific contrary language.

In the context of the present application, the terms "lower" and "upper" are used interchangeably with the terms "inflow" and "outflow", respectively. Thus, for example, the lower end of the valve is its inflow end and the upper end of the valve is its outflow end.

As used herein, the term "proximal" refers to a position, direction, or portion of a device that is closer to the user and further away from the implantation site. As used herein, the term "distal" refers to a position, direction, or portion of a device that is further away from the user and closer to the implantation site. Thus, for example, proximal motion of a device is motion of the device away from the implantation site and toward the user (e.g., out of the patient's body), while distal motion of the device is motion of the device away from the user and toward the implantation site (e.g., into the patient's body). The terms "longitudinal" and "axial" refer to an axis extending in the proximal and distal directions, unless otherwise expressly defined.

In view of the many possible embodiments to which the principles of the disclosure may be applied, it should be recognized that the illustrated embodiments are only preferred examples of the invention and should not be taken as limiting the scope of the disclosure. Rather, the scope of the disclosure is defined by the following claims.

We claim:

1. A prosthetic valve delivery assembly, comprising:
- a prosthetic valve comprising an expandable frame having a plurality of apices at one end of the frame; and
- a delivery apparatus, comprising:
  - a cord-retaining device comprising an annular body having an outer surface, the cord retaining device further comprising a plurality of circumferentially spaced tabs extending radially outwardly from the outer surface of the annular body;
  - one or more slideable release members extending through the cord-retaining device;
  - a plurality of separate cords, each comprising a first end portion comprising a first loop having a first opening and a second end portion comprising a second loop having a second opening;
  - a sheath advanceable over the prosthetic valve to retain the prosthetic valve in a radially compressed state, wherein the sheath can be retracted relative to the prosthetic valve to permit radial expansion of the prosthetic valve to a radially expanded state;
  - wherein each cord extends through an aperture in one of the apices or extends around one of the apices of the frame, wherein the first loop of each cord extends around one of the tabs, and wherein the second end portion of each cord is retained by one of the slideable release members extending through the second opening of the second loop;

wherein the one or more slideable release members can be moved axially relative to the second end portions of the cords to release the second end portions of the cords from the one or more slideable release members, thereby allowing the prosthetic valve to be released from the delivery apparatus.

2. The assembly of claim 1, wherein the cords have a multi-stranded construction formed from a plurality of strands of material.

3. The assembly of claim 2, wherein the multi-stranded construction is a braided construction.

4. The assembly of claim 2, wherein the multi-stranded construction is a twisted construction.

5. The assembly of claim 2, the multi-stranded construction is a whip stitch construction.

6. The assembly of claim 2, wherein the plurality of strands of material are made from a polymer.

7. The assembly of claim 6, wherein the polymer is an ultra-high molecular weight polyethylene.

8. The assembly of claim 2, wherein the plurality of strands of material are flexible wires.

9. The assembly of claim 1, wherein each tab comprises a proximal portion spaced radially outward from the outer surface of the annular body, wherein the proximal portion has a radially inwardly facing surface and a radially outward facing surface, wherein a radially extending gap is defined between the radially inward facing surface of the proximal portion of the tab and the outer surface of the annular body, and wherein the first loop extends within the gap.

10. The assembly of claim 1, wherein the first opening of each cord encircles one of the tabs.

11. A prosthetic valve delivery assembly, comprising:

a prosthetic valve comprising an expandable frame having a plurality of apices at one end of the frame; and a delivery apparatus comprising;

a cord-retaining device along a distal end portion of the delivery apparatus;

one or more slideable release members extending through the cord-retaining device;

a sheath advanceable over the prosthetic valve to retain the prosthetic valve in a radially compressed state, wherein the sheath can be retracted relative to the prosthetic valve to permit radial expansion of the prosthetic valve to a radially expanded state;

a plurality of separate cords, each cord comprising a first end portion comprising a first loop having a first opening and a second end portion comprising a second loop having a second opening, wherein each cord comprises a multi-stranded construction formed from a plurality of strands of material, wherein the first loop comprises first and second separately braided sections on opposite sides of the first opening, and the second loop comprises first and second separately braided sections on opposite sides of the second opening, wherein the first separately braided section of the first loop comprises a first set of strands of the plurality of strands that are braided together to form a plurality of first picks and the second separately braided section of the first loop comprises a second set of strands of the plurality of strands that are braided together to form a plurality of second picks;

wherein each cord extends through an aperture in one of the apices or extends around one of the apices of the frame with the first loop of the cord retained on the cord-retaining device and the second loop of the cord retained by one of the slideable release members extending through the opening in the second end portion of the cord; and wherein the one or more slideable release members can be moved axially relative to the second end portions of the cords to release the second end portions of the cords from the one or more slideable release members, thereby allowing the prosthetic valve to be released from the delivery apparatus.

12. The assembly of claim 11, wherein the cord-retaining device comprises a plurality of tabs and the first end portion of each cord has an opening and is retained on one of the tabs extending through the opening of the first end portion of the cord.

13. The assembly of claim 11, wherein each cord comprises a fully braided section extending from the first loop to the second loop.

14. The assembly of claim 13, wherein the plurality of strands of material are braided together along the fully braided section of each cord and each of the first and second separately braided sections of each loop are formed by two or more strands of the plurality of strands.

15. A method for delivering a prosthetic heart valve, comprising:

inserting a distal end portion of a delivery apparatus into the vasculature of a patient, wherein a prosthetic heart valve is retained in a radially compressed state within a sheath of the delivery apparatus along the distal end portion, wherein the prosthetic heart valve has a plurality of apices at one end thereof and is releasably connected to a cord-retaining device of the delivery apparatus by a plurality of separate cords, wherein the cord-retaining device comprises a proximal portion and a distal portion axially spaced from the proximal portion, wherein the delivery apparatus comprises one or more slideable release members extending through the proximal portion and the distal portion of the cord-retaining device, and wherein each cord comprises a first end portion and a second end portion having an opening, wherein each cord comprises a multi-stranded construction formed from a plurality of strands of material, wherein each cord extends through an aperture in one of the apices or extends around one of the apices of the frame with the first end portion of the cord retained on a respective tab of the proximal portion of the cord-retaining device and the second end portion of the cord retained by one of the slideable release members extending through the opening in the second end portion of the cord, wherein the second end portion of each cord is retained on one of the slidable release members at a location between the proximal portion and the distal portion of the cord-retaining device and distal to the first end portion of the cord;

advancing the distal end portion of the delivery apparatus and the prosthetic heart valve through the patient's vasculature to a location at or adjacent a selected implantation location;

retracting the sheath of the delivery apparatus relative to the prosthetic heart valve to deploy the prosthetic heart valve from the sheath; and wherein deploying the prosthetic heart valve from the sheath allows a distal end of the prosthetic heart valve to radially expand while a proximal end of the prosthetic heart valve remains connected to the cord-retaining device by the cords, such that the distal end of the prosthetic valve expands to a larger diameter than the proximal end of the prosthetic valve.

16. The method of claim 15, further comprising retracting the one or more slideable release members relative to the cords to release the second end portions of the cords, thereby allowing the prosthetic heart valve to be released from the delivery apparatus.

17. The method of claim 15, wherein the multi-stranded construction is a braided construction.

18. The method of claim 15, wherein the first end portion of each cord has a respective opening that receives a protrusion of the cord-retaining device to retain the cord relative to the cord-retaining device.

* * * * *